United States Patent [19]

Klass et al.

[11] Patent Number: 4,567,748
[45] Date of Patent: Feb. 4, 1986

[54] ON-LINE LINEAR TONOMETER

[76] Inventors: Carl S. Klass, 25 Sunflower Dr., Hauppauge, N.Y. 11788; Ernest F. Geiger, 716 Pine Tree Ct., Port Jefferson, N.Y. 11777

[21] Appl. No.: 632,390
[22] Filed: Jul. 19, 1984
[51] Int. Cl.$^4$ .................. G01N 33/96; G01N 33/50
[52] U.S. Cl. ........................... 73/1 G; 422/50; 422/68; 422/99; 436/11; 436/16
[58] Field of Search ............... 73/1 G; 436/11, 16, 436/68; 422/50, 68, 99, 101, 102

[56] References Cited

U.S. PATENT DOCUMENTS

| | | | |
|---|---|---|---|
| 3,639,830 | 2/1972 | Harnoncourt | 422/68 X |
| 3,885,414 | 5/1975 | Reville | 73/1 G |
| 3,920,396 | 11/1975 | Schuy | 436/68 |
| 3,973,915 | 8/1976 | Raffaele et al. | 436/68 X |
| 4,108,607 | 8/1978 | Pearson et al. | 436/11 X |
| 4,209,300 | 6/1980 | Thibault | 73/1 G X |
| 4,251,483 | 2/1981 | Carroll | 422/68 |
| 4,256,461 | 3/1981 | Wallace et al. | 436/68 X |
| 4,301,117 | 11/1981 | Smernoff | 436/11 X |
| 4,358,424 | 11/1982 | Weber et al. | 422/50 X |
| 4,403,038 | 9/1983 | Asakura et al. | 436/11 X |
| 4,424,276 | 1/1984 | Clark et al. | 436/68 X |

OTHER PUBLICATIONS

"Quality Control in Blood pH and Gas Analysis by Use of a Tonometered Bicarbonate Solution and Duplicate Gas Analysis"; Clin. Chem.; vol. 27; No. 10; pp. 1761–1764; Robert W. Burnett; 1981.

Primary Examiner—Stewart J. Levy
Assistant Examiner—Tom Noland
Attorney, Agent, or Firm—Leonard Belkin

[57] ABSTRACT

A tonometer having vessels for producing and maintaining multi-levels of tonometerd aqueous buffered solutions and whole blood available for use in the quality controlling of a blood-gas analyzer. A water bath maintains all vessels at a predetermined temperature and gas mixtures are supplied at a very low rate thereby permitting continuous operation of the tonometer.

8 Claims, 7 Drawing Figures

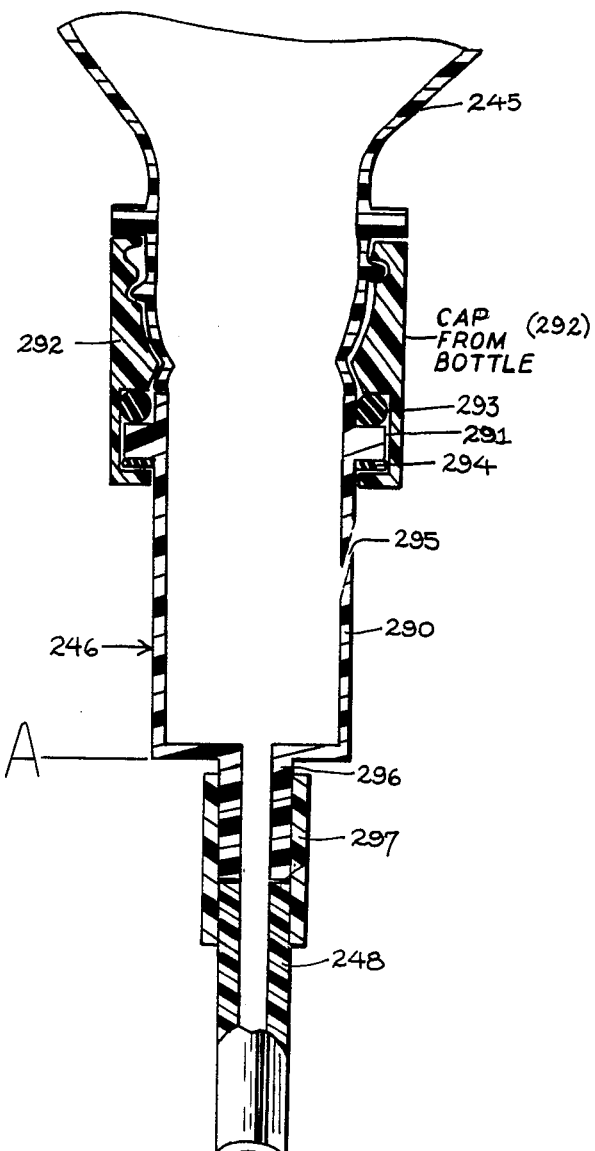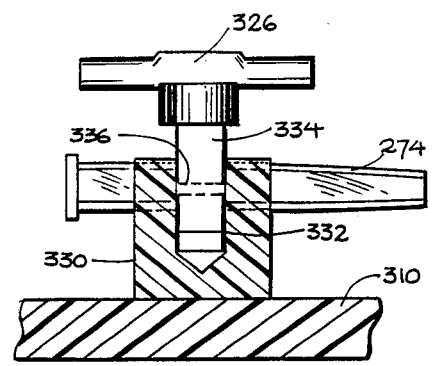

ON-LINE LINEAR TONOMETER

BACKGROUND OF THE INVENTION

This invention relates to an on-line linear tonometer and more particularly to apparatus and method for providing accurately tonometered aqueous buffer solutions and whole blood on a continuous basis for use in the quality control of blood gas analyzers.

The measurement of pH and the partial pressures of oxygen ($pO_2$) and carbon dioxide ($pCO_2$) in blood samples is routinely performed in hospitals, laboratories and other institutions because of the significance of such information in relation to a patient's cardiovascular, respiratory and metabolic status.

These measurements are carried out by blood gas analyzers which may be manual, semiautomatic, or completely automatic or automated in operation. The fully automatic units are becoming increasingly popular because of their ability to conduct measurements rapidly, typically up to twenty samples an hour, and accurately, provided calibration is properly maintained.

Checking of calibration, that is, quality control, in an automated blood analyzer can be expensive and inconvenient. For example, the most popular type of automated blood gas analyzer in use today relies on three electrode systems to determine levels of pH, $pCO_2$, and $pO_2$. There is a separate electrode system for each of the above factors. As the blood sample is exposed in turn to each electrode an electrical output is produced which is proportional to the factor to which that electrode is sensitive.

Calibration of these olood gas analyzers involves adjusting the interpretation of actual electrode output based on the measurement of samples with known levels of pH, $pCO_2$, and $pO_2$. Such samples are provided by the manufacturer in the form of pH buffers and calibrated gas. These substances are inserted into the analyzers at intervals specified by the manufacturer with the readout of the machine adjusted accordingly to reflect the known values. Typically, a manufacturer might indicate intervals of two hours of use for a two-point calibration (adjusting the electrode response at two levels) and every thirty minutes of operation for a one-point calibration (electrode response at one level).

The performance of blood gas analyzers, which are capable of making very precise measurements, frequently is subject to degradation of accuracy due to a variety of factors such as: coating of the electrodes with blood proteins, loss of internal electrolyte from electrodes, plugging of internal pathways by minute blood clots, etc. It is essential therefore to repeatedly analyze samples of known concentration throughout the active work period. The analysis of known samples is termed quality control testing. This invention is a device for producing such a quality control product for use in such testing.

With regard to the tonometered samples employed to quality control the blood gas analyzer, it is obvious that tonometered whole blood would be preferred, but blood s relative instability, its unreliability as a pH reference, procurement difficulties, and biohazard potential make it a less than acceptable fluid for general use. As a consequence, there have been developed certain liquids capable of holding $CO_2$ and $O_2$ in solution in known amounts, and a variety of such solutions are available packaged in one-time-use vials or ampules.

The basic techniques involved in preparing tonometered buffered solutions or whole blood are described and illustrated in a journal article entitled "Quality Control in Blood pH and Gas Analysis by Use of a Tonometered Bicarbonate Solution and Duplicate Blood Analysis" appearing in Clinical Chemistry, Vol. 27, No. 10, 1981, pages 1761-1764. A prepared mixture of $CO_2$, $O_2$, and $N_2$ is bubbled up through the buffered solution until equilibration occurs at which time the solution is ready for use. As noted in the article, there are severe problems associated with the described arrangements.

An institution employing the blood gas analyzer can either prepare its own tonometered liquid samples for quality controlling its machine, or, as is more commonly the case, purchase the tonometered samples packaged in one-time use ampules as noted above. Because of the costs involved and other problems, hospitals, laboratories, and other institutions employing blood gas analyzers generally do not prepare their own samples for quality control. Equipment to prepare large amounts of tonometered solutions and package them in single use ampules for storage is prohibitive in cost and not practical for an institution not having a factory environment.

However, the cost of utilizing purchased ampules containing tonometered liquid samples for quality control is also quite high. In a typical hospital with an automated blood gas analyzer requiring nine calibrations a day, the cost of the ampules containing the tonometered solutions runs about two dollars each or between six and over seven thousand dollars per year. If more than nine assays a day are required, the cost will run even higher. Where there is present more than one analyzer it can be seen that the costs to the institution of maintaining its blood gas analyzers can be a substantial factor in providing medical services.

Another drawback in the use of ampules has to do with their questionable accuracy, which is in the range of 5-10%, probably due to the effects of packaging, shipping, and storage. Ampules, however, are currently the method of choice for quality control due to the lack of a better alternative.

In U.S. Pat. No. 4,358,424 to Weber et al which is directed to the tonometering of blood plasma, there is shown online tonometering apparatus which is excessively complex and expensive in construction due to the built-in frit construction, the double syringes for each channel, and the relatively complicated gas supply configuration. In addition the use of open vessels creates potential contamination. It appears also that Weber et al contemplates intermittent operation of the device since apparently a 40-minute waiting period is specified for equilibration so that it is not available at all times for use.

SUMMARY OF THE INVENTION

The present invention makes it possible for an institution utilizing a blood gas analyzer requiring tonometered solutions and/or whole blood for quality control to produce its own tonometered solutions and whole blood for calibration at a cost which is far less than the present cost of existing procedures and with a degree of reliability and accuracy not heretofore attainable.

In accordance with the principles of this invention, in a preferred embodiment, apparatus is provided in which a buffered aqueous solution is maintained in a state of equilibration by the continuous bubbling of a prepared preselected mixture of gases. A unique arrangement is incorporated which permits tapping of the equilibrated solution whenever it is desired to quality control the blood gas analyzer. Added to the buffered solution is an agent which reduces by an order of magnitude the size of the gas bubbles rising in the solution which increases the effectiveness of the bubbling action in maintaining a state of equilibration to such an extent that bubbling rates can be reduced substantially from what has been required heretofore thereby making it practical and cost effective to maintain the bubbling action on a continuous basis having the solution always available for use.

In another embodiment of this invention there is provided a unique arrangement for tonometering whole blood so that the technician or analyst can when desired check the blood gas analyzer with whole blood as the controlling sample.

The blood tonometering apparatus can be combined in a single operating unit containing several buffered solutions all being equilibrated with a different predetermined mixture of gases, or levels (i.e., level 1, level 2, and level 3) so that all the controlling samples, both buffered solutions and whole blood are immediately available for use.

It is thus a principal object of this invention to provide apparatus for the production of standard tonometered buffered solutions for use in the quality control of blood gas analyzers.

Another object of this invention is apparatus for equilibrating buffered solutions with gas mixtures at improved efficacy and efficiency.

Still another object of this invention is apparatus for the tonometering of whole blood.

Other objects and advantages of this invention will hereinafter become obvious from the following detailed description of preferred embodiments of this invention.

BRIEF DESCRIPTION OF THE DRAWINGS

FIG. 5 is a section through the valve for automatically maintaining the level of buffered solution in its bubbling vessel.

FIG. 6 is a section through the stopcock where samples are withdrawn.

DETAILED DESCRIPTION OF THE PREFERRED EMBODIMENTS

Figure 1:
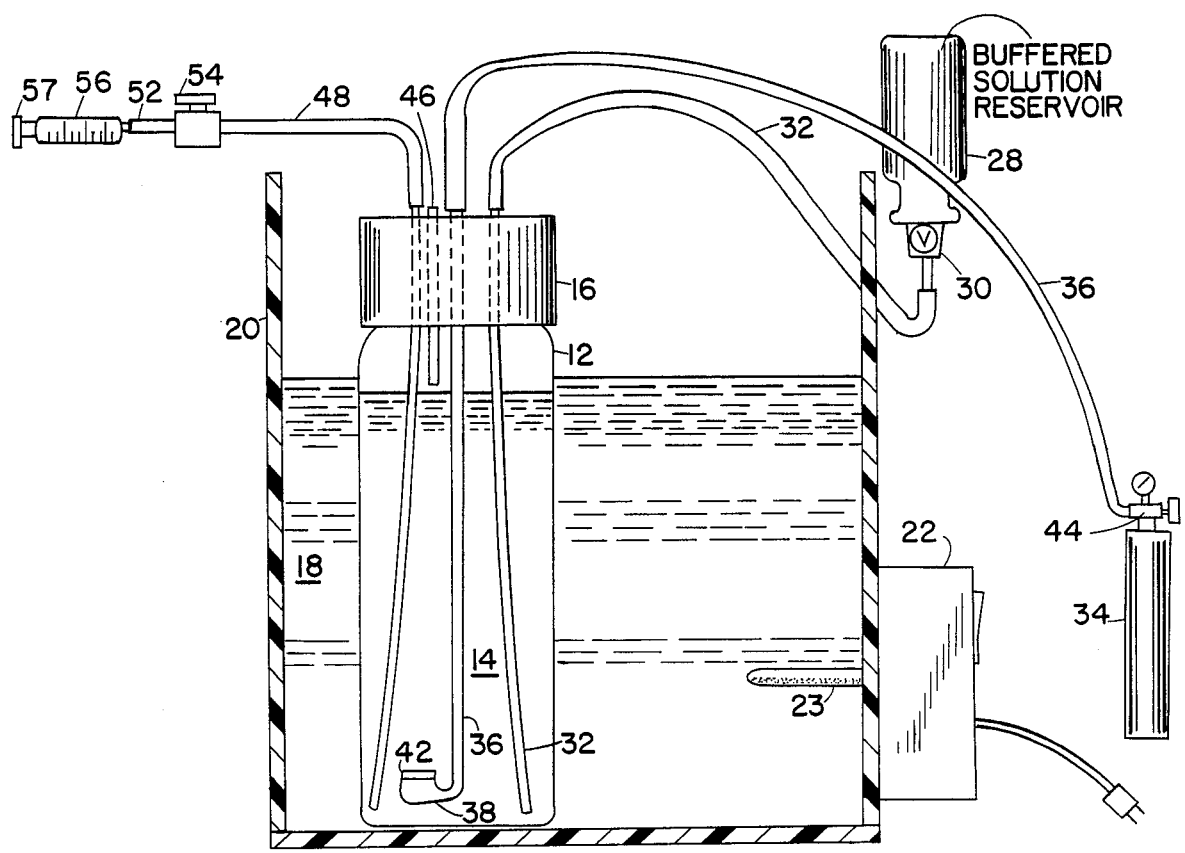
FIG. 1 is an elevation view in section, partially schematic, of one embodiment of this invention for tonometering a buffered solution.

Referring to FIG. 1, there is illustrated a tonometry bottle or vessel 12 containing buffered solution 14 and having a tightly screwed on cap 16. Vessel 12 is immersed in a water bath 18 within a container 20 having a heater 22 with a heating element 23 to maintain solution 14 at the desired temperature, typically 37° C.

Buffered solution is supplied to vessel 12 from a reservoir 28 by gravity feed through a line or conduit 32 terminating adjacent the bottom of vessel 12. A valve 30 in line 32 permits vessel 12 to be filled when the level drops a predetermined amount due to removal of sample for analysis. The capacity of vessel 12 should be at least such that the replacement of solution does not significantly affect the state of equilibration of the solution within this vessel. This requires a relatively large size vessel. Typically vessel 12 will have a capacity of 500 ml. but filled with about 400 ml. of buffer solution to prevent overfilling.

One buffered solution, available commercially, is an aqueous solution of bicarbonate, sodium phosphate with the addition of an agent consisting of tetrabutylammonium iodide (TBAI) which has the effect of reducing the size of the bubbles of the gas mixture bubbled through the solution as will be hereinafter described.

In order to equilibrate solution 14 with a gas of known composition of $pCO_2$ and $pO_2$, and thus produce the tonometered solution, tank 34 containing the known composition of these gases, with the balance nitrogen, under pressure, is connected by way of tubing 36 into vessel 12 terminating near the bottom thereof in an open gas dispersion reservoir 38 closed off with a medium pore size glass frit 42 to feed the gas into the solution. Valve 44 permits adjustment of the rate of gas flow. It has been found that with the use of the buffered solution herein described with the addition of TBAI that bubble size is too small to measure by conventional means, and that, estimated from observation, typical bubble size appears to be predominantly no more than about one-fiftieth of a millimeter in diameter, or $2 \times 10^{-3}$ cm. These bubbles form a cloud as they leave frit 42 and there is vigorous internal circulation of the bubbles within solution 14 before the gases leave vessel 12 through vent 46. It has been found that gas flow rates in the range of 2–4 ml. per minute are adequate to maintain solution 14 in a fully tonometered state although a flow rate of 5–8 ml. per minute may be maintained to insure that there is adequate equilibration at all times.

For withdrawing some of tonometered solution 14 for use in running a control of a blood gas analyzer as hereinabove described, there is provided tubing 48 extending out of vessel 12 and terminating at 52. A A valve or stopcock 54 is provided to open and close tubing 48. The hub portion of a syringe 56 is inserted into the opening at 52 into stopcock 54. The latter is then opened and a small amount, typically 3 ml., of solution is pulled into syringe 56 by withdrawing plunger 57. Plunger 57 is then pushed in to force some solution down tubing 48 into vessel 12. Plunger 57 is then retracted once again until the desired amount of solution is withdrawn into syringe 56 as indicated by the calibration thereon and then valve 54 is closed. This procedure avoids taking a sample from the dead space within tube 48 and insures that a fresh and completely equilibrated solution is withdrawn. In other words, a single syringe may be employed to freshen and withdraw a selected volume of solution for quality control.

The general technique which has been described hereinabove with respect to the tonometering of buffered aqueous solutions is applicable to whole blood except for some important differences which will hereinafter be described.

The advantage of being able to use tonometered whole blood in a quality control program is that a matrix exactly the same as a patient sample will test all facets of the blood-gas analyzer's system, to wit, its hydraulics, flush, electrodes, etc. Blood, tonometered at 37° C., will permit the analyst to calculate and test for theoretical values of $pCO_2$ and $pO_2$ in whole blood. Therefore, the accuracy of the blood gas analyzer can be tested as well as its reproducibility using aqueous buffers However, as is understood in the art, tonometered whole blood is useless for the determination of pH since salt concentrations vary widely from sample to sample.

Figures 2, 2A:
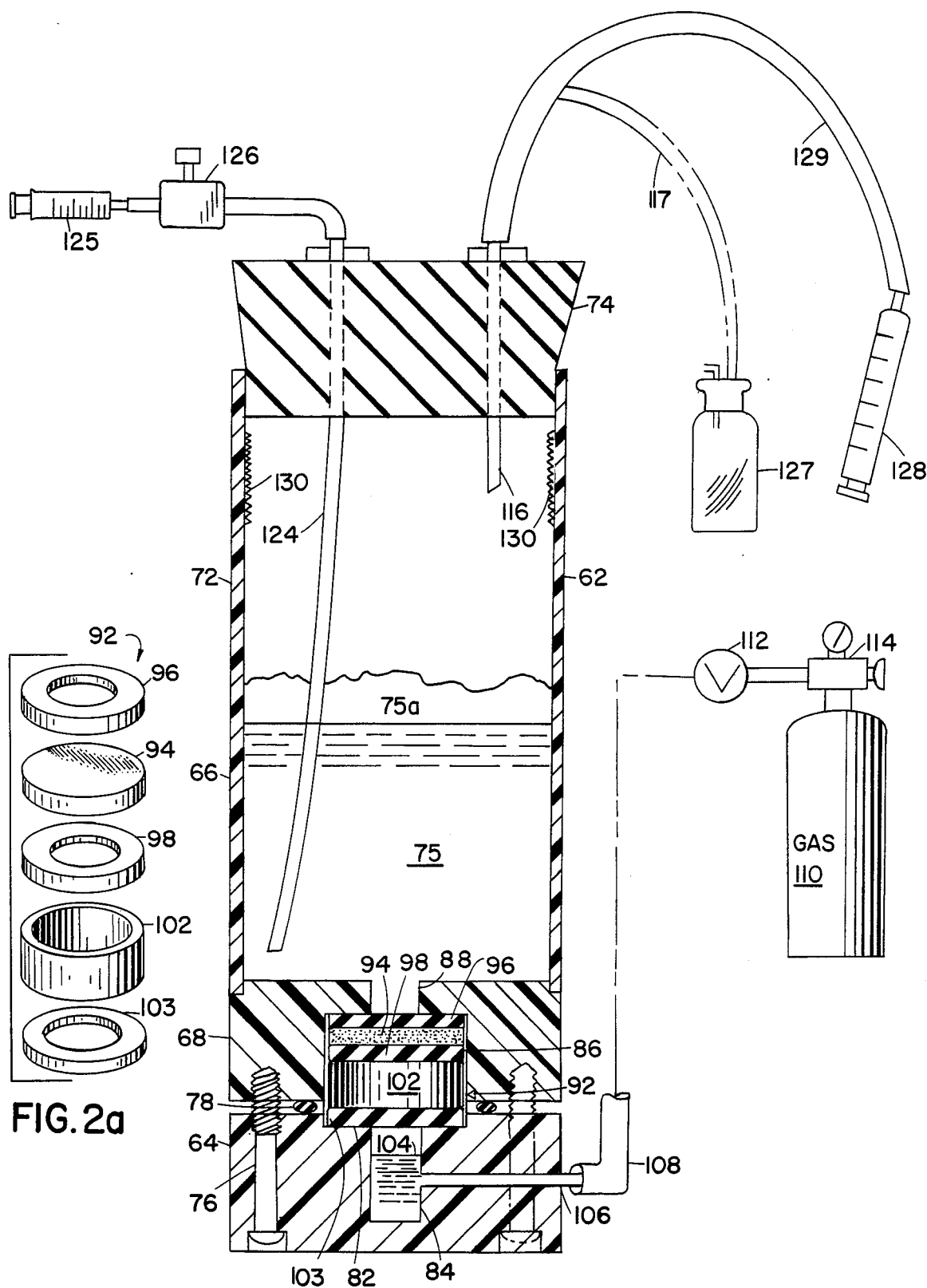
FIG. 2 is an elevation view in section, partially schematic, of another embodiment of this invention for tonometering whole blood.
FIG. 2a is an exploded view of the frit assembly used in FIG. 2.

An arrangement for tonometering whole blood in accordance with the principles of this invention is shown in FIGS. 2 and 2a. Blood equilibration vessel 62 is cylindrical and consists of a solid lower section 64 of lucite or similar material and a separate upper section 66 which has a solid base 68 of lucite or similar material and a hollow open top glass cylinder 72 extending upwardly. A rubber stopper 74 closes off the top of glass cylinder 72 thereby forming a closed vessel containing whole blood 75 with a froth 75a.

It will be seen that lower section 64 is attached to base 68 by a plurality of countersunk, annularly arranged screws 76 and separated by a compressed O-ring 78 which provides sealing.

Lower section 64 is provided with a circular depression 82 with a smaller diameter well 84. Base 68 has a matching, oppositely facing chamber 86 with a hole 88 communicating with the interior of glass cylinder 72.

Supported on depression 82 is microporous frit assembly 92 consisting of a glass frit 94 sandwiched between a pair of annular gaskets 96 and 98 and a cylindrical glass spacer 102 supported on a gasket 103.

Within well 84 is distilled or demineralized water 104 to act as a humidifier for the gas to be bubbled through.

Extending through the side wall of lower section 64 is a stainless steel tube 106 connected by tubing 108 to gas cylinder 110 through a valve 112 to adjust the rate of gas flow and a stopcock 114. Within tank 110 there is provided the reference mixture of $O_2$, $CO_2$, and $N_2$.

In order to insert the water into well 84, tubing 108 is withdrawn from tube 106, vessel 62 tilted and water injected by syringe through tube 106. Then vessel 62 is righted after tube 106 and tubing 108 are reconnected.

Referring to the upper part of vessel 62, it is seen that stopper 74 is provided with tubes 116 and 124, the latter terminating near the bottom of cylinder 72.

The purpose of tubing 124 is to permit removal of tonometered blood 122 by syringe 125 connected to stopcock 126 in the same manner as was explained in connection with vessel 12 in FIG. 1, except that it may be desirable to cycle the blood in the dead space by syringe 125 at least five times. Whole blood 75 is inserted into vessel 62 from syringe 128 by way of tubing 129 and tube 116. The latter is disconnected from syringe 128 after insertion of blood. Tubing 117 is then connected to tubing 116 to carry the waste gas and air froth to waste tank 127. Vessel 62 would be immersed in a temperature controlled water bath as previously described in connection with FIG. 1.

In the operation of the apparatus just described, gas from tank 110 is bubbled through humidifying water 104 up through frit 94 to produce bubbles and rise through blood 75 reaching equilibration over a period of time, that is, blood 75 reaches a stable level of gas in solution. The water bath (not shown) is maintained at a suitable temperature such as 37° C. It has been found that the reference gas mixture can be changed by switching tanks and permitting a thirty-minute period to establish equilibration with the new gas mixture.

It is understood in the art that to reduce the formation of froth 75a, grease 130 may be used to coat tne inside of glass near the top of cylinder 72 and if desired the bottom face of cork 74.

Figure 3:
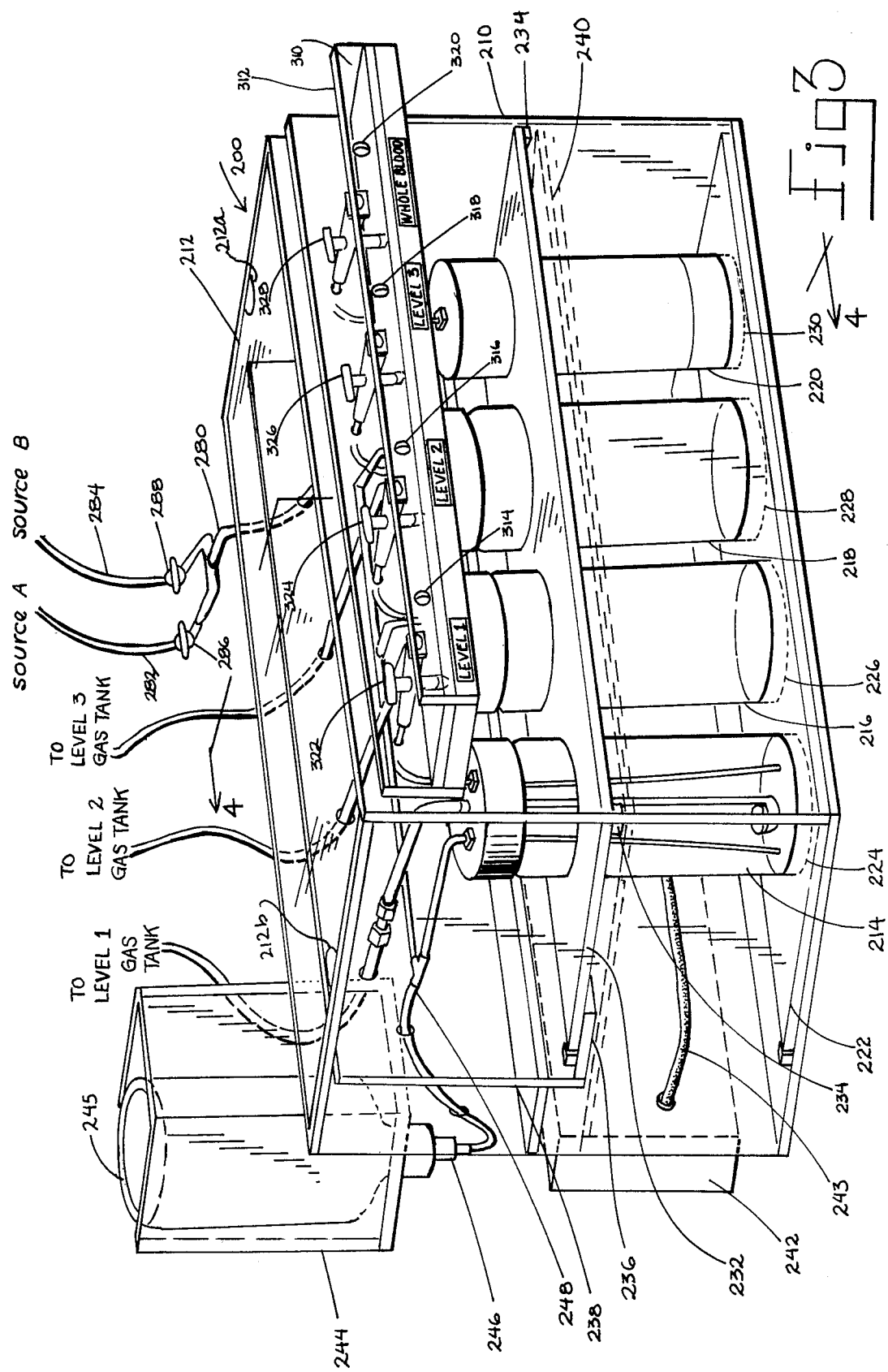
FIG. 3 is an isometric view, partially schematic, of an embodiment of this invention combining buffered solutions and whole blood in one apparatus.
Figure 4:
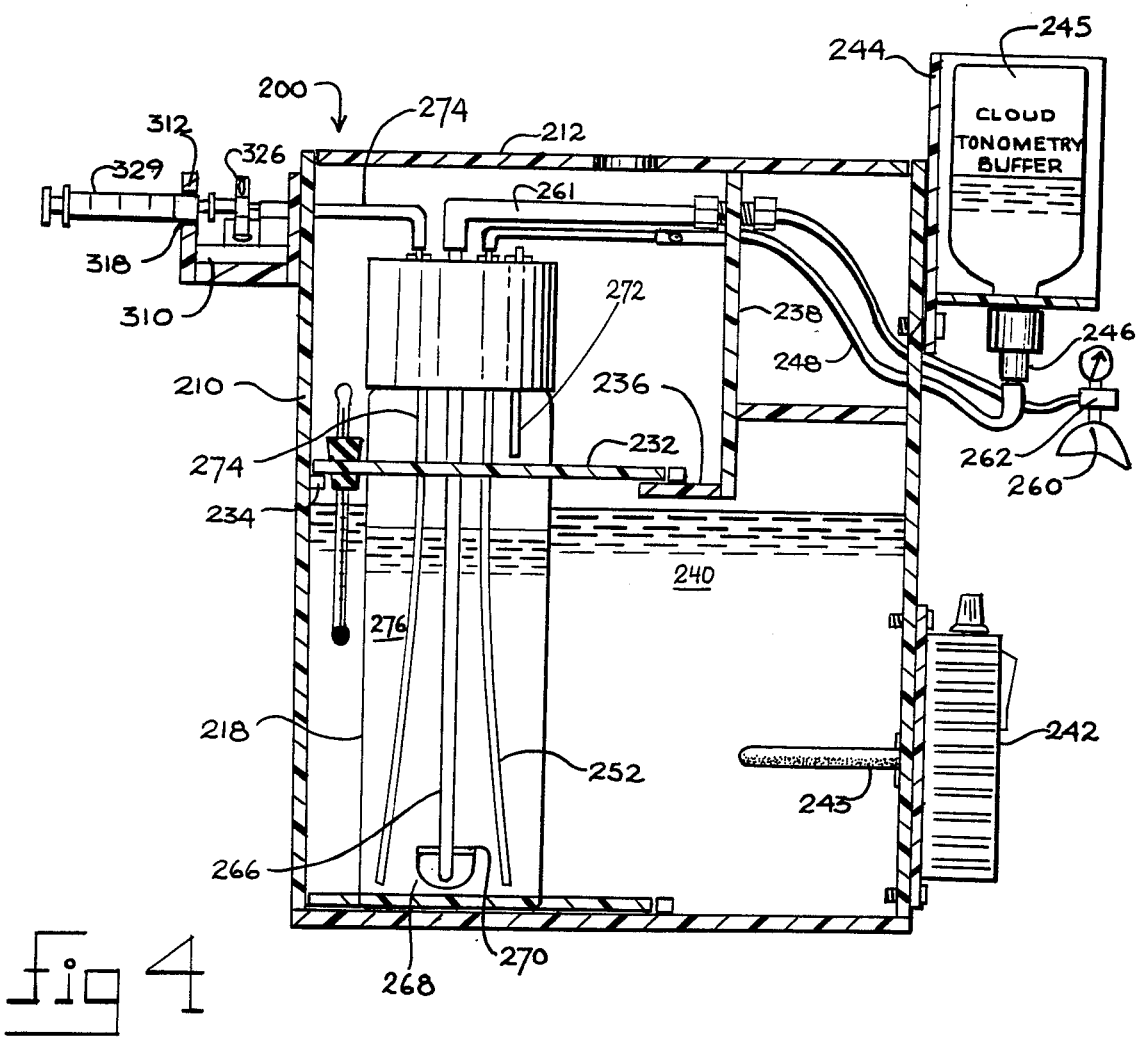
FIG. 4 is a section along 4—4 of FIG. 3 and showing in partially schematic form some of the features of that embodiment.

A complete system incorporating the principles of this invention utilizing both the above described tonometering assemblies for providing up to three point control (that is, checking electrode response at three levels) while also offering whole blood calibration is illustrated in FIGS. 3 and 4.

Referring to FIGS. 3 and 4, whole blood-aqueous buffer tonometer 200 consists of a container 210 having a removable cover 212 having openings 212a and 212b both of which typically are made of plexiglass which is transparent so that the apparatus within can be observed while in operation and which at the same time has excellent thermal insulating characteristics so that maintenance of the water bath temperature therein is effective by reducing thermal gradients and efficient by reducing the amount of energy required.

Within container 210 there are four cylindrical vessels 214, 216, 218, and 220. Vessels 214, 216, and 218 are identical to vessel 12 shown in FIG. 1 except that each one is supplied with a different mixture of $pO_2$, $pCO_2$, and $N_2$ from a separate gas tank, and these mixtures are referred to herein as level 1, level 2, and level 3, respectively, as shown by labels on the front of container 210, for the benefit of the analyst. Vessel 220 is identical to vessel 62 shown in FIG. 2.

A rectangular base plate 222 on the bottom is provided with circular openings 224, 226, 228, and 230 to accommodate the bottoms of each of the preceding vessels, respectively. An upper removable plate 232 supported by shoulders 234 and a platform 236 has aligned openings through which each of the vessels is inserted thereby maintaining them each firmly in an upright position. An upright member 238 supports the various tubes and connectors as will be described below. As illustrated, a water bath 240 fills container 210 up to an appropriate level and a through-the-wall electric heater 242 with a heating element 243 insures that the water and hence the contents of the various vessels will be maintained at a proper temperature.

A reagent reservoir holder 244 supports the buffered solution in an inverted reagent reservoir or bottle 245 for use in vessels 214, 216, and 218.

A valve 246 is attached to bottle 245 and tubing 248 which leads to vessels 214, 216, and 218.

As seen in FIG. 4, for vessel 218 in particular, tubing 248 from valve 246 delivers buffered solution to vessel 218 through a tube 252.

Each vessel 214, 216, and 218 has its own gas supply since each receives a different mixture. Thus, vessel 218 receives its gas mixture from tank 260 through tubing 261 having a valve 262 to control the rate of flow into dispersion tube 266 and reservoir 268 which has a frit 270 as previously described in connection with FIG. 1. Valve 262 may be located so as to be convenient for the analyst. Vessel 218 is also provided with a vent 272, and a tube 274 for the withdrawal of tonometered solution 276. Vessels 214 and 216 are of identical construction except for the supply of level 1 and level 2 gas mixtures.

Vessel 220, containing whole blood to be tonometered, identical to vessel 62 shown in FIG. 2, is connected by way of tubing 280 and branches 282 and 284 to separate sources of two different gas mixtures referred to herein as source A and source B, respectively, it being understood that each source would comprise a tank containing the appropriate gas mixture of $O_2$, $CO_2$, and the balance $N_2$. As noted in connection with the disscussion of FIG. 2, the gas mixture can be changed by the the analyst, by opening either one of the stopcocks 286 or or 288 provided a period of time is permitted to elapse, such as twenty minutes, to permit equilibration with the new mixture to take place. As in FIG. 2, vessel 220 would be supplied with a waste line connected to a waste bottle because of the possible presence of froth.

Valve 246 may be designed to automatically maintain the level of buffered solution within vessels 214, 216, and 218. Referring to FIG. 5 for details of the former, it will be seen that valve 246 consists of a cylinder 290 with a flange 291 mounted within a cap 292 threaded on bottle 245. An O-ring 293 above flange 291 and a gasket 294 below flange 291 insures sealing. An opening 295 in the sidewall of cylinder 290 slanted downward permits air to enter and fill the space within bottle 245 above the level of solution therein.

The bottom of cylinder 290 terminates in a smaller diameter cylindrical section 296 aligned with tubing 24 supplying buffered solution to vessels 214, 216, and 218. A sleeve 297 insures sealing where tubing 248 joins cylindrical section 296.

It has been found that with the arrangement just described the level within each of vessels 214, 216, and 218 will be maintained at A shown in FIG. 5 so that bottle 245 should be mounted so as to have line A located at the level desired within the aforementioned vessels. However, automatic valve 246 is optional and may be replaced with a simple shut-off valve for each of the branches of tubing going to the vessels and the analyst can replace solution in each vessel after some use. The operation of automatic valve 246 as herein described is believed to depend on the surface tension of the solution within bottle 245.

In order to permit convenient and sanitary withdrawal of accurately measured amounts of buffered solution or blood from container 210, the latter is provided with a platform 310 projecting from its front wall and having an upright member 312 with circular cutouts 314, 316, 318, and 320 opposite each of and aligned with four stopcocks 322, 324, 326, and 328 respectively. On platform 310 there is the termination of a tubular member for each vessel having a stopcock, such as that shown for vessel 218 where withdrawal tube 274 is provided with a stopcock 326, the open mouth of which is is aligned exactly with opening 318.

Thus, when the analyst wishes to extract a sample from vessel 218 he need only place the hub of syringe 329 through opening 318 into the open mouth of stopcock 326, and then open the latter Opening 318 insures proper alignment. Each opening in upright member 312 matches exactly the outside diameter of the barrel of the syringe and proper alignment avoids almost entirely the possibility that air can enter the syringe or tube. The openings also provide protection for the syringes so that lateral forces cannot break either the syringes or stopcocks.

As shown in FIG. 6, syringe 329 is held securely in place by a block of lucite 330 or similar material by means of a vertical hole 332 drilled to accommodate snugly the body 334 of stopcock 326 and a horizontal hole 336 in body 334 through which the solution passes. A single elongated block 330 accommodates all four stopcocks corresponding to one each for each buffer solution equilibration vessel and another for the whole blood equilibration vessel. The entire block is securely attached to the platform 310 by any convenient means such as screws (not shown).

In the operation of the apparatus just described water bath temperature is maintained at some acceptable value such as 37° C. Each of the vessels for levels one, two, and three is filled about three quarters full with the buffered solution, and gas flow is then adjusted to some low value, preferably 5–8 ml per min. Such a low flow rate is possible because of the very small bubbles formed as noted above. Because of the very low gas flow rates, tonometer 200 may be left in operation continuously so that it is always available to extract a sample.

In using the syringe to extract samples, because of the so-called dead space in the tubing leading from the stopcock on platform 310 into each vessel, it is necessary to withdraw some solution into the syringe, pump it back down the tubing, and by repeating one or more times before withdrawing the syringe the analyst is assured of obtaining a thoroughly equilibrated sample. Whole blood vessel 220 may be withdrawn at any time to be cleaned in preparation for a fresh supply of whole blood without disturbing the operation qf the other vessels.

An important feature of this invention is the ease of removing any of the vessels for cleaning, and if desired, this can be done while not disturbing the other vessels.

Another important feature of this invention is that the analyst can select the size of the sample he wishes. Thus he takes only the exact amount required without wasting any tonometered solution, whereas, when ampules are employed most of the solution is discarded.

Another advantage of this invention is that the tonometered solution is always fresh. When solution from an ampule is utilized there are problems with regard to shelf-life, temperature at which storage is conducted, and probable air contamination because strict control over post-opening sample time cannot be maintained.

A buffered aqueous solution which has been found to function well in this invention was composed of disodium hydrogen phosphate, 47.2 m mol, potassium dihydrogen phosphate, 11.8 m mol, and sodium hydrogen carbonate, approximately 22.4 m mol, to provide a pH of 7.383±0.005 when equilibrated at 37° C. to a $pCO_2$ of 40 mm Hg. Methyl-p-hydroxy benzoate and propyl-p-hydroxybenzoate were added at 0.2%, respectively, to inhibit bacterial and fungal growth. TBAI was added to the buffer to produce a concentration of 50 mg/liter. The TBAI is effective between 25–100 mg/liter and is useful with other buffered solutions to produce small bubble size. However, excess TBAI may cause froth to form in the equilibration vessel when excessive gas flow is present.

It is thus seen that there has been provided unique apparatus and method for providing tonometered solutions and whole blood for the quality control of blood gas analyzers.

While only certain preferred embodiments of this invention have been described, it is understood that many variations are possible without departing from the principles of this invention as defined in the claims which follow.

What is claimed is:

1. Apparatus for producing on a continuous basis a tonometered solution for use in the quality control of a blood gas analyzer comprising:
   a. a vessel containing an aqueous buffered solution containing tetrabutyl-ammonium iodide in the range of 25–100 mg/liter;

b. means for supplying a reference gas consisting of a known mixture of $CO_2$, $O_2$, and $N_2$ under pressure to said vessel;

c. gas dispersing means within said vessel for receiving said gas mixture including a reservoir with a glass frit to bubble said gas mixture into said solution;

d. means for controlling the rate of gas flow in the range of 5-8 ml per minute resulting in establishing and maintaining equilibration of said solution; and e. means for permitting utilization of a single syringe for freshening and withdrawing as needed a selected amount of said solution required for use in said analyzer without interrupting gas flow thereby permitting equilibration to be maintained during withdrawal.

2. The apparatus of claim 1 in which said bubbles being formed are predominantly no more than $2 \times 10^{-2}$ mm in diameter.

3. Apparatus for tonometering whole blood for calibrating a blood-gas analyzer comprising:

a. a vessel for containing said whole blood;

b. a supply of a known gas mixture of $CO_2$, $O_2$, and $N_2$;

c. dispersing means within said vessel beneath and in contact with said blood for receiving said gas mixture and discharging bubbles of the latter into and for equilibrating of said whole blood;

d. said dispersing means comprising a well formed in the bottom of said vessel containing a reservoir of water, frit means within the bottom of said vessel immediately above said well in contact on its upper surface with said whole blood, and means to pass said gas mixture through the water in said well for humidifying said gas mixture and through said frit means; and e. means for permitting utilization of a single syringe for freshening and withdrawing the exact size sample of said whole blood required for use in said blood gas analyzer while maintaining gas flow and without interrupting equilibration of said blood.

4. Apparatus for preparing tonometered samples of buffered solution and whole blood for use in the quality control of a blood gas analyzer comprising means for establishing a liquid bath and aid in maintaining said bath at a pre-determined temperature, at least one vessel immersed in said bath containing an aqueous buffered solution containing tetrabutyl-ammonium iodide in the range of 25-100 mg/liter, means for supplying a known gas mixture of $CO_2$, $O_2$, and $N_2$ to said vessel, gas dispersing means within said vessel for bubbling said gas mixture up through said solution, means for controlling the rate of gas mixture flow in the range of 5-8 ml. per minute, another vessel immersed in said bath containing whole blood, means for supplying said whole blood vessel with a known gas mixture of $CO_2$, $O_2$, and $N_2$, dispersing means within said whole blood vessel for discharging bubbles of said gas into said whole blood, said dispersing means comprising a well formed in the bottom of said whole blood vessel containing a reservoir of water, frit means immediately above said well in contact on its upper surface with said whole blood, means to pass said gas mixture through the water in said well for humidifying said gas mixture, and means for permitting utilization of a single syringe for freshening and withdrawing the exact size sample from each of said vessels for use in said blood gas analyzer.

5. The apparatus of claim 4 having multiple vessels containing aqueous buffered solutions immersed in said bath and means for supplying said multiple vessels with different mixtures of $CO_2$, $O_2$, and $N_2$ thereby permitting multiple level calibration of said blood gas analyzer with tonometered buffered solutions.

6. The apparatus of claim 5 having means to deliver buffered solutions automatically to the solution vessels when the level of said solution declines by a predetermined amount as a result of withdrawal, said vessel having sufficient capacity such that replacement of solution does not significantly adversely affect the state of equilibration of the solution within said vessel.

7. The apparatus of claim 6 in which said means for permitting utilization of said syringe includes tubing extending from each of said vessels, valve means for permitting flow out of each set of tubing, and means for insuring alignment of said syringe as it is inserted into the outlet of said valve means thereby preventing leakage or contamination of said equilibrated buffered solution or blood.

8. The apparatus of claim 7 in which said alignment means comprises an extended member having openings aligned with said valve means to accommodate and support a hub of said syringe.

* * * * *